United States Patent [19]

Witkowski et al.

[11] Patent Number: 4,634,689

[45] Date of Patent: Jan. 6, 1987

[54] PHOSPHINYLALKANOYL IMINO ACIDS

[75] Inventors: Joseph T. Witkowski, Morris Township, Morris County; Michael F. Czarniecki, Westfield, both of N.J.

[73] Assignee: Schering Corporation, Kenilworth, N.J.

[21] Appl. No.: 793,078

[22] Filed: Oct. 31, 1985

[51] Int. Cl.$^4$ .................. A61K 31/54; C07D 285/32; C07D 285/26; C07F 9/65

[52] U.S. Cl. .......................... 514/80; 514/7; 514/210; 514/212; 514/222; 514/82; 544/2; 544/3; 544/5; 544/8; 544/13; 540/481; 540/542

[58] Field of Search .................. 544/13, 2, 3, 5, 8; 260/243.3; 514/222, 80, 7, 210, 212

[56] References Cited

U.S. PATENT DOCUMENTS

| | | | |
|---|---|---|---|
| 4,337,201 | 6/1982 | Petrillo | 548/413 |
| 4,338,435 | 7/1982 | Haugwitz | 544/13 |
| 4,384,123 | 5/1983 | Petrillo | 548/409 |
| 4,427,665 | 1/1984 | Karanewsky et al. | 424/200 |
| 4,431,644 | 2/1984 | Smith et al. | 544/13 |
| 4,431,645 | 2/1984 | Smith et al. | 544/13 |
| 4,444,765 | 4/1984 | Karanewsky et al. | 548/409 |
| 4,452,791 | 6/1984 | Ryono et al. | 548/409 |
| 4,468,396 | 8/1984 | Magatti | 544/13 |
| 4,468,519 | 8/1984 | Krapcho | 548/409 |
| 4,555,506 | 11/1984 | Karanewsky et al. | 514/91 |
| 4,555,579 | 11/1985 | Rovnyak | 548/409 |
| 4,556,655 | 12/1985 | Andrews et al. | 544/13 |
| 4,560,680 | 12/1985 | Ryono et al. | 514/82 |

FOREIGN PATENT DOCUMENTS 63896B 8/1985 European Pat. Off. .
3410847A 3/1983 Fed. Rep. of Germany .

Primary Examiner—John M. Ford
Attorney, Agent, or Firm—Anita W. Magatti; Stephen I. Miller; Gerald S. Rosen

[57] ABSTRACT

Phosphinylalkanoyl imino acids useful in the treatment of hypertension are disclosed.

21 Claims, No Drawings

PHOSPHINYLALKANOYL IMINO ACIDS

SUMMARY

The present invention relates to phosphinylalkanoyl imino acids. Compounds of this invention are useful as antihypertensives, in the treatment of congestive heart failure, and in the treatment of glaucoma. Compounds of this invention may have diuretic and/or angiotensin converting enzyme (ACE) inhibitory activity.

DETAILED DESCRIPTION

More particularly, this invention relates to compounds represented by the following formula I $$Z-CH(R)-(CH_2)_n-P(R^1)(=O)-CH_2-C(=O)-X \quad \text{I}$$

wherein
X is

IIa: $-N-C(R^4)(-)-CH(R^5)-COR^8$

IIb: $-N-C(-)(CH_2)_s-Y-Y-COR^8$

IIc: $-N-C(-)(CH_2)_t-COR^8$

IId: $-N-C(-)-(CH_2)_p-C_6H_4-(CH_2)_q-COR^8$ or

IIe: $-N(R^6)-C(R^7)-COR^8$

Y is $-S-$ or $-O-$;

Z is

IIIa: $R^2R^3N-S(O_2)-C_6H_3(R^{13})-NH-CH(R^2)-$ or

IIIb: $R^2HNO_2S-C_6H_3(R^{13})-S(O_2)-N(R^3)-CH(-)-NH-B-$

A is $-(CH_2)_m-C_6H_4-(CH_2)_r-D-$, $-(CH_2)_x-C(=O)-NH-$ or a bond;

B is $-(CH_2)_m-C_6H_4-(CH_2)_r-D-$, $-(CH_2)_r-C(=O)-NH-$ or a bond;

D is $-C(=O)-NH-$ or a bond;
m, n, and r are independently 0–4;
x is 1–4;
p and q are independently 0 or 1, provided that the sum of p and q is 1 or 2;
s is 2 or 3;
t is 1–3;
R is hydrogen, lower alkyl, halogen-substituted lower alkyl, cycloloweralkyl, $-(CH_2)_u-$cycloloweralkyl, or $-(CH_2)_v-C_6H_5$ wherein u is 1–4 and v is 0–4;
$R^1$ is hydroxy, alkoxy having from 1 to 8 carbon atoms, phenylloweralkoxy, allyloxy, $R^9-Q_w-(CH_2)_y-O-$, wherein Q is oxygen or sulfur, w is 0 or 1 and y is 2 to 4, $$-OCH(R^{10})-OCO-\text{alkyl}$$

wherein the alkyl has from 3 to 8 carbon atoms, $$-OCH(R^{10})OCO-\text{phenyl}$$

wherein the phenyl may be substituted with group T defined below, 1-glyceryl, $-O-$ phthalidyl or $-OCH_2-CH(O-CO-R^{11})(O-CO-R^{12})-CH_2$ (dioxolane)

$R^2$ is R or heterocycloloweralkyl;
$R^3$ is hydrogen or lower alkyl;
$R^4$ and $R^5$ are independently hydrogen, lower alkyl or cycloloweralkyl, or $R^4$ and $R^5$ together with the carbon atoms to which they are attached form a 5- or 6-membered ring;
$R^6$ and $R^7$ are independently hydrogen, lower alkyl or cycloloweralkyl, or $R^6$ and $R^7$ together with the nitrogen and carbon atoms to which they are attached form a 4-, 6-, 7- or 8-membered ring;

$R^8$ is $R^1$, amino, hydroxylamino, mono- or disubstituted amino wherein the substituents are lower alkyl, phenyl or phenylloweralkyl, and wherein the phenyl may be substituted with group T defined below;

$R^9$ is phenyl, substituted phenyl wherein the substituents are chosen from group T, 1-naphthyl or 2-naphthyl;

T is halogen, hydroxy, trifluoromethyl, lower alkoxy, lower alkyl, 2-furanyl, 3-furanyl, 2-thienyl, 3-thienyl, phenyl and substituted phenyl wherein the substituents are chosen from halogen, hydroxy, trifluoromethyl, lower alkoxy or lower alkyl;

$R^{10}$ is hydrogen or alkyl having from 1 to 8 carbon atoms;

$R^{11}$ is hydrogen, lower alkyl, unsubstituted or substituted phenyl and substituted or unsubstituted phenylloweralkyl wherein phenyl may be substituted by group T;

$R^{12}$ is hydrogen or lower alkyl;

$R^{13}$ is chloro or trifluoromethyl;

or a pharmaceutically acceptable salt thereof.

When X is formula IIa, a preferred group is characterized by $R^4$ and $R^5$, together with the carbons to which they are attached, forming a five or six-membered ring. When X is formula IIb, compounds wherein each Y is sulfur and s is 2 are preferred. For compounds wherein X is IId, a preferred group is represented by values of 0 and 1 for p and q, respectively. Formulae IIa and IIb represent preferred structures for group X.

Compounds wherein Z is formula IIIa are preferred, with those wherein A is

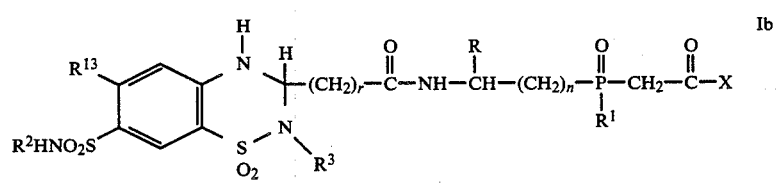

being more preferred. Especially preferred are those compounds wherein Z is of formula IIIa and wherein m and r are not zero. When Z is formula IIIa and A is not a bond, n is preferably 0 or 1. Also preferred are compounds wherein the phenyl group is joined in the paraposition. Another group of preferred compounds are those wherein $R^{13}$ is chloro.

Also preferred are compounds wherein Z is formula IIIb wherein B is a bond. More preferred are compounds wherein Z is of formula IIIb, B is a bond and $R^2$ is hydrogen; especially preferred are those compounds wherein B is a bond, $R^2$ is hydrogen and n is 5.

Examples of preferred compounds of formula I are as follows:

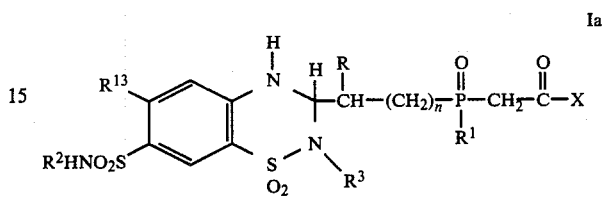

Ia especially wherein $R^2$ is benzyl, $R^3$ is methyl and n is 4;

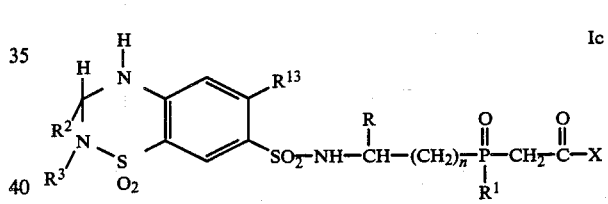

Ib especially wherein $R^2$ is benzyl, $R^3$ is methyl, and n is 4;

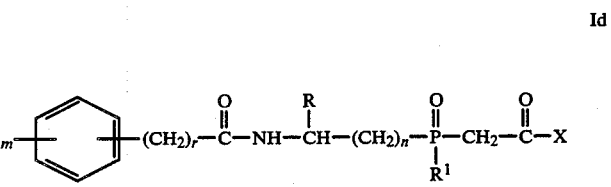

Ic especially wherein R is phenyl, $R^2$ is n-butyl or phenylethyl, $R^3$ is hydrogen or methyl, n is 3, and X is N-cyclopentyl glycine (i. e., X is of formula IIe wherein $R^6$ is cyclopentyl, $R^7$ and $R^8$ are hydrogen );

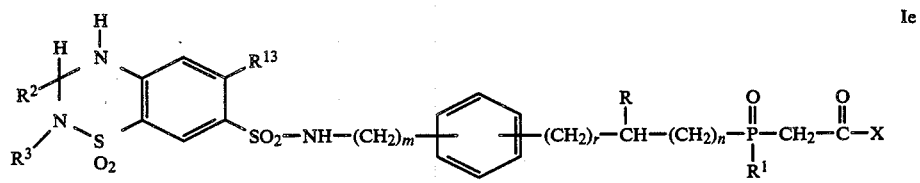

Id especially wherein r is 0, n is 1 or 3 and m is not zero

Ie especially wherein m is not 0 and the sum of r and n is 3 or 4.

As used herein, "lower alkyl" means straight or branched chain hydrocarbon radicals of from 1 to 6 carbons, e.g. methyl, ethyl, propyl, isopropyl, butyl, tbutyl, pentyl and hexyl. Similarly, "lower alkoxy" means straight or branched alkoxy radicals having from 1 to 6 carbon atoms, e.g. methoxy, ethoxy, propoxy, butoxy, isobutoxy, pentoxy and hexyloxy. "Halogen" means fluorine, chlorine and bromine. "Heterocyclo" radicals include 5- or 6-membered aliphatic or aromatic rings containing 3 to 5 carbon atoms and 1 to 3 heteroatoms selected from nitrogen, sulfur and oxygen, e.g. imidazolyl, thiazolyl, pyridyl and morpholino; all positional isomers (e.g. 2-, 3- or 4-pyridinyl) are contemplated.

Compounds of the instant invention may include various stereoisomers. Preferred stereoisomers are those in which the absolute configuration at carbon atoms adjacent to both a nitrogen and a carbonyl group corresponds most closely to the absolute configuration of α-amino acids.

The compounds of this invention form salts with various inorganic and organic acids and bases which are also within the scope of the invention. Such salts include ammonium salts, alkali metal salts, e.g. sodium and potassium salts, and alkaline earth metal salts, e.g. calcium and magnesium salts. Salts with organic bases also may be prepared, e.g., N-methylglucamine, lysine and arginine salts. Those compounds with a basic substituent e.g., pyridyl, may form salts with organic and inorganic acids, e.g., HCl, HBr, $H_2SO_4$, $H_3PO_4$, methanesulfonic acid, toluenesulfonic acid, maleic acid, fumaric acid and camphorsulfonic acid. The non-toxic pharmaceutically acceptable salts are preferred, although other salts are also useful, e.g., in isolating or purifying the product. The alkali metal salts are preferred, especially the sodium salt.

The salts may be formed by conventional means, as by reacting the free acid or base forms of the product with one or more equivalents of the appropriate base or acid in a solvent or medium in which the salt is insoluble, or in a solvent such as water which is then removed in vacuo, or by exchanging the cations of an existing salt for another cation on a suitable ion exchange resin.

Compounds of the invention may be made by methods known in the art. Examples of methods of preparing compounds represented by formulae Ia-e are as follows:

Compounds of formula Ia (i.e. wherein Z is of formula IIIb and B is a bond) can be prepared by condensing an acid of formula IV with an amino acid derivative of formula V:

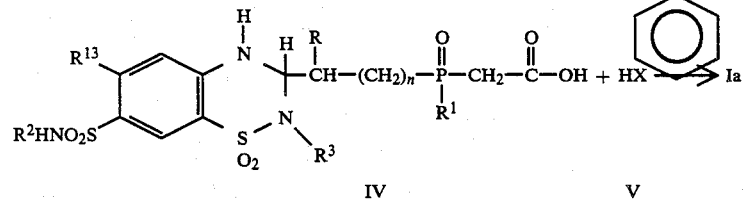

wherein R, $R^1$, $R^2$, $R^3$, $R^{13}$, X and n are as defined above. The reaction is carried out in an inert solvent such as dimethylformamide (DMF) in the presence of a condensing agent such as 1,1'-carbonyldiimidazole. The reaction is preferably carried out in an inert atmosphere at a temperature of 0°–25° C.

Compounds of formula IV can be prepared by known methods, for example as shown in the following flow diagram for compounds wherein R, $R^2$, $R^3$ and $R^8$ are hydrogen and n is 0:

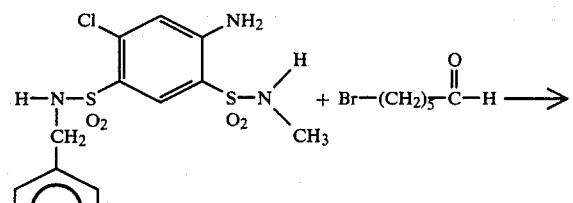

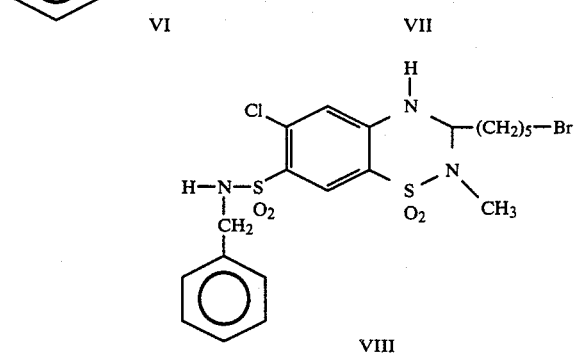

VIII + $(CH_3CH_2O)_2$—P—$CH_2$—COOEt ⟶

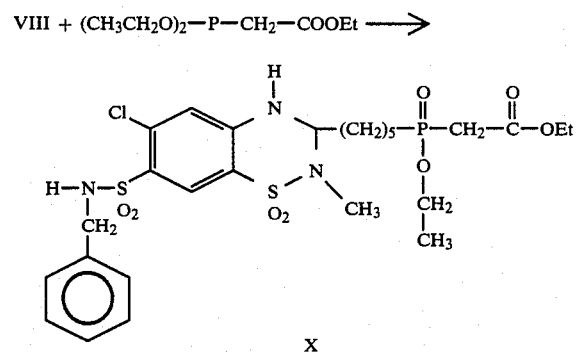

X $\xrightarrow{Br-Si(CH_3)_3}$

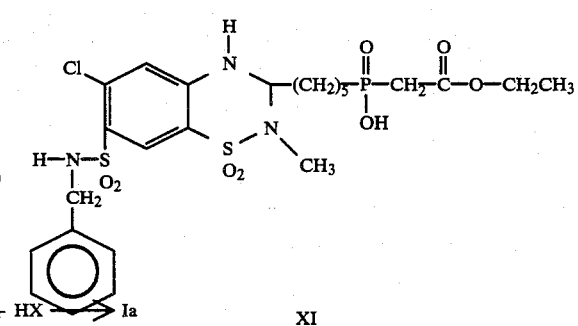

XI 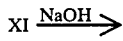

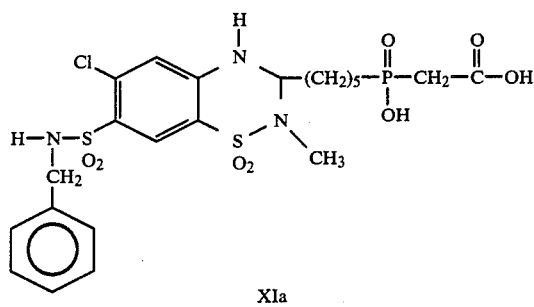

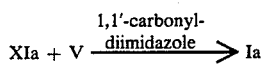

Compounds of formula V, VI, VII and IX are known in the art or may be prepared by well known methods.

Compounds of formula Ib (wherein Z is of formula IIIb and B is

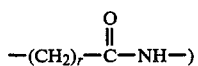

may be prepared by condensing a benzothiadiazinyl acid of formula XII with an aminoalkylphosphinyl compound of formula XIII:

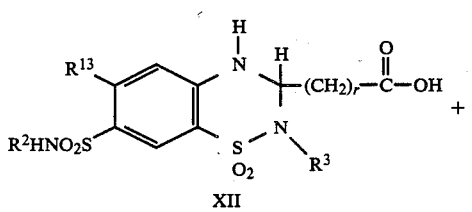

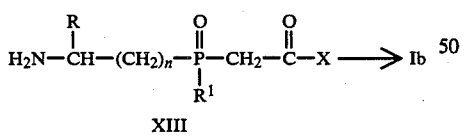

wherein R, $R^1$, $R^2$, $R^3$, $R^{13}$, r, n and X are as defined above, under conditions similar to those described for preparing compounds of formula Ia.

Compounds of formulae XII and XIII are both known in the art, or may be prepared by readily available methods.

To prepare compounds of formula Ic (wherein Z is of formula IIIa and A is a bond) a benzothiadiazinyl sulfonyl chloride of formula XIV may be reacted with an aminoalkylphosphinyl compound of formula XIII:

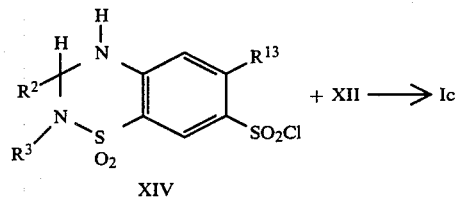

wherein $R^2$, $R^3$ and $R^{13}$ are as defined above. Reaction conditions are again similar to those for preparing compounds Ia.

Compounds of formula XIV may be prepared from known starting materials using procedures well known in the art. For example, when $R^2$ is phenylethyl, $R^3$ is hydrogen and $R^{13}$ is chloro, a sulfonyl chloride of formula XIVa may be obtained by reacting a disulfonyl chloride of formula XV with aqueous ammonia at low temperature (dry-ice-acetone bath) in a solvent such as 1,2-dimethoxyethane (DME) in the presence of a base such as triethylamine to obtain a sulfonamide of formula XVI, followed by reaction of the sulfonamide with phenyl propanal in a solvent such as DME and in the presence of an acid such as p-toluenesulfonic acid:

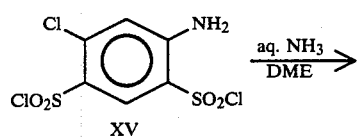

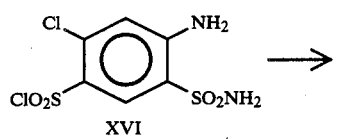

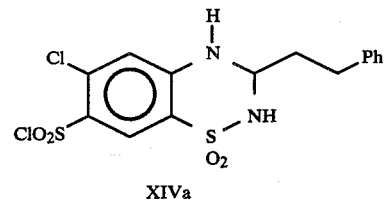

For compounds of formula Id (i.e. wherein Z is of formula IIIa and A is

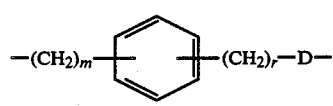

and wherein D is

an acid of formula XVII may be reacted under the conditions described above with an aminoalkylphosphinyl compound of formula XIII:

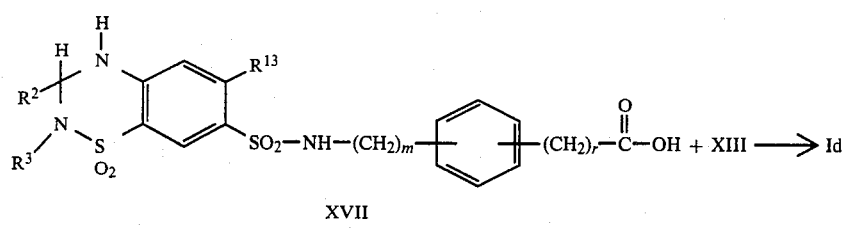

XVII wherein $R^2$, $R^3$, $R^{13}$, m and r are as defined above.

Compounds of formula XVII may be prepared by known methods, for example compounds of formula XVIIa wherein m is 1, r is 0, the phenyl group is joined in the 1,4 position, $R^{13}$ is chloro and $R^2$ and $R^3$ are as defined above, may be prepared as follows:

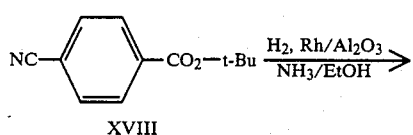

XVIII

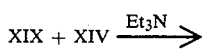

XIX + XIV $\xrightarrow{\text{Et}_3\text{N}}$

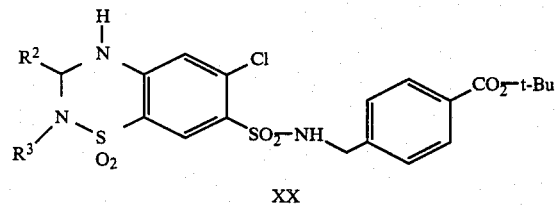

XX

XX $\xrightarrow{\text{TFA, HOAc}}$

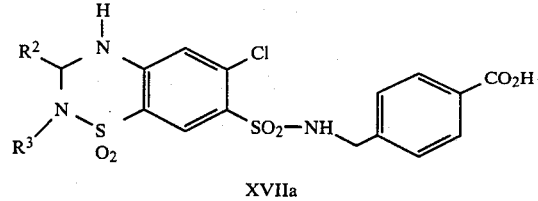

XVIIa

Compounds of formula Ie (i.e. wherein Z is of formula IIIa, A is

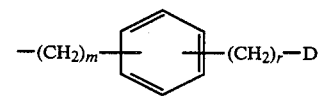

and wherein D is a bond) may be prepared by condensing an acid of formula XXI with an amino acid of formula V, again under conditions similar to those described for compounds of formula Ia:

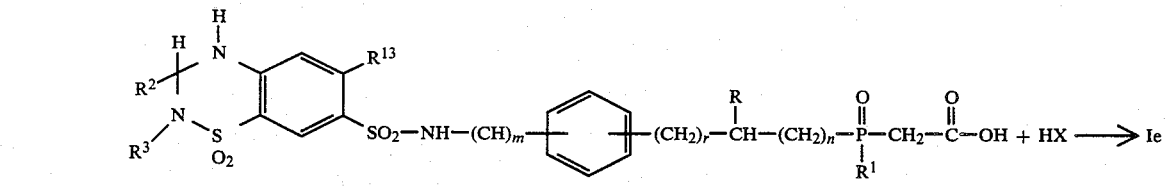

XXI           V wherein R, $R^1$, $R^2$, $R^3$, $R^{13}$, X, m, n and r are as defined above.

Acids of formula XXI may be prepared from known starting materials using known methods. For example, compounds of formula XXIa wherein R, $R^1$ and $R^8$ are hydrogen, $R^{13}$ is chloro, the phenyl group is in the para configuration, r is 0, m is 1, n is 4 and $R^2$, $R^3$ and X are as defined above may be prepared as follows:

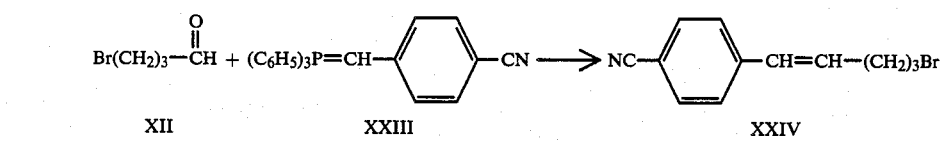

XII         XXIII           XXIV

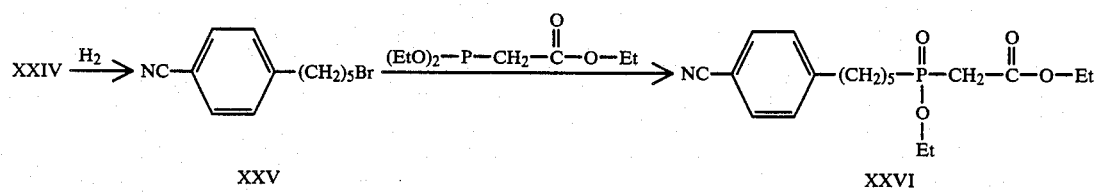

XXV           XXVI

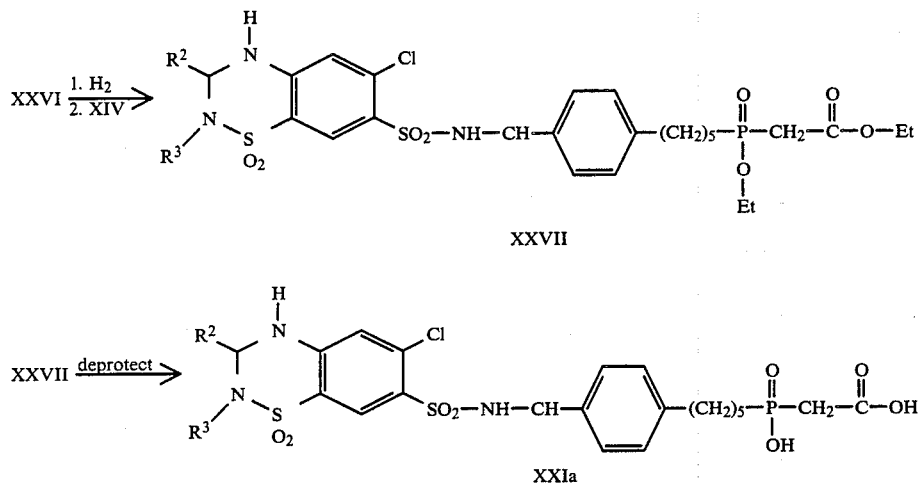

Compounds of formulae XXII and XXIII are known or may be prepared by known methods.

The known coupling methods above may include phosphinyl group protection during the coupling reaction, for example with protecting groups such as alkyl, e.g. ethyl, and benzyl groups, followed by their removal to yield compounds of formula I. Furthermore, the $COR^8$ function wherein $R^8$ is OH may be protected by removable ester groups such as benzyl, ethyl, t-butyl, trimethylsilylethyl and the like.

The following preparations and examples further illustrate the preparation of compounds of this invention.

PREPARATION 1

6-CHLORO-3,4-DIHYDRO-3-(2-PHENYLETHYL)-2H-1,2,4-BENZOTHIADIAZINE-7-SULFONYL CHLORIDE, S,S-DIOXIDE

A. Dissolve 5 g 4-amino-6-chloro-1,3-benzenedisulfonyl chloride in 20 ml DME, cool in a dry-ice/acetone bath and add 2 ml triethylamine. Add dropwise 25% ammonium hydroxide in water (1 ml) in DME (4 ml), stir in a dryice acetone bath for 1 hour, allow to warm to room temperature, and stir for 90 min. Dilute the resultant reaction mixture with ethyl acetate, wash with 4% aq HCl, water and brine, dry over $MgSO_4$ and evaporate to obtain a solid residue.

B. Combine 13.6 g of the sulfonamide prepared in Step A, 6.57 g phenyl propanal, 25 ml DME and 20 mg p-toluenesulfonic acid and stir at room temperature under $N_2$ for 3 hours. Evaporate the solvent, dissolve the resultant residue in 250 ml ethyl acetate, wash with 100 ml sat'd aq. $NaHCO_3$ and 100 ml brine, then dry over $MgSO_4$, filter and evaporate the solvent to obtain the crude title compound. Purify the crude residue by precipitation in $CH_2Cl_2$; mp. 167.0°–167.5° C.

PREPARATION 2

3-BUTYL-6-CHLORO-3,4-DIHYDRO-2H-1,2,4-BENZOTHIADIAZINE-7-SULFONYL CHLORIDE, S,S-DIOXIDE

Combine 90 g of the sulfonamide prepared in Preparation 1, Step A, 36 ml valeraldehyde, 0.3 g p-toluenesulfonic acid and 400 ml DME and stir at room temperature for 20 hours. Evaporate the solvent, extract and precipitate the resultant residue as described in Preparation 1, Part B to obtain the title compound, m.p. 161°–162° C.

PREPARATION 3

CIS,SYN-OCTAHYDRO-1H-INDOLE-2(S)-CARBOXYLIC ACID, PHENYLMETHYL ESTER

A. Dissolve 27.0 g of ethyl indole-2-carboxylate in 250 ml of trifluoroacetic acid. Add 2.05 g of platinum oxide and hydrogenate the mixture at 50 lb/in² at room temperature. Filter the mixture and concentrate the filtrate in vacuo to give a residue. Suspend the residue in ether and treat with cold dilute sodium hydroxide solution. Dry the organic layer over magnesium sulfate and concentrate it to give octahydro-1H-indole-2-carboxylic acid, ethyl ester, a pale yellow oil.

B. Dissolve 116 g 10-d-camphorsulfonic acid in 1 liter of warm ethyl acetate and add a solution of 86 g of the product of part A in 1 liter of ethyl acetate. Allow the mixture to crystallize, heat to reflux, cool to room temperature, and filter. Recrystallize the filter cake from a mixture of 500 ml isopropanol and 1800 ml ethyl acetate, filter and dry the crystals to obtain cis,synoctahydro-1H-indole-2(S)-carboxylic acid, ethyl ester, d-10-camphorsulfonate, m.p. 192°–193° C.

C. Heat the product of Part B (107.6 g) and d-10-camphorsulfonic acid (6.35 g) in benzyl alcohol (270 ml) at 105° C. under vacuum for 6 hours or until TLC (silica, elute neutralized sample with ethyl ether) indicates reaction is complete. Pour the resultant residue into ethyl ether, seed and stir to obtain a precipitate. Filter the precipitate, wash with ethyl ether (2×500 ml) and dry the resultant residue under vacuum to obtain cis,-syn-octahydro-1H-indole-2(S)-carboxylic acid, phenylmethyl ester, d-10-camphorsulfonate, m.p. 114°–118° C.

D. Suspend the product of Part C (150 g) in ethyl ether (1500 ml), add 1N aqueous NaOH (300 ml) and stir until the solid dissolves. Separate the organic layer and wash the aqueous layer with ethyl ether (2×200 ml). Combine the organic layer, wash with brine, dry over $Na_2SO_4$ and evaporate the solvent to obtain the title compound.

PREPARATION 4

CIS,SYN-OCTAHYDRO-1H-INDOLE-2(S)-CARBOXYLIC ACID, (1,1-DIMETHYLETHYL)ESTER

A. Dissolve the product of Preparation 3 (77 g) in absolute ethanol (900 ml), add 4% Pd/C (10 g) and hydrogenate at room temperature at an initial pressure of 60 p.s.i. After 3 hours, filter off the catalyst and wash with hot methanol. Evaporate the combined filtrate and wash in vacuo, triturate the resultant residue in ethanol (100 ml), chill the solution, then filter and air dry the resultant precipitate to obtain a residue, m.p. 269°–270° C.

B. Suspend the product of Part A in dioxane (400 ml) and conc. $H_2SO_4$ (40 ml), add isobutylene (300 ml) and shake in a Parr shaker for 28 hours. Pour the resultant reaction mixture into 50% aqueous NaOH (150 ml) in 500 ml ice water and extract with ethyl ether (3×500 ml). Wash the combined organic extracts with water, then brine. Dry the organic layer over $Na_2SO_4$ and evaporate the solvent to obtain the title compound.

EXAMPLE 1

N-[[5-[[6-CHLORO-3,4-DIHYDRO-2-METHYL-7-[(PHENYLMETHYL)AMINOSULFONYL]-2H-1,2,4-BENZOTHIADIAZIN-3-YI]PENTYL]HYDROXYPHOSPHINYL]ACETYL]-N-CYCLOPENTYLGLYCINE, S, S-DIOXIDE

(A)
4-Amino-6-Chloro-3-(Methylaminosulfonyl)Benzenesulfonyl Chloride

Cool a solution of 4-amino-6-chloro-1,3-benzenedisulfonyl chloride (32.3 g) in tetrahydrofuran (THF, 150 ml) to −78° C. under a nitrogen atmosphere. Add a solution of 1.45 Molar methylamine in benzene (100 ml) containing triethylamine (10.1 g) dropwise with stirring over 45 minutes. After the addition is complete, stir at room temperature for 3 hours. Vacuum evaporate the solvent and partition the residue between ethyl acetate (EtOAc) (500 ml) and 10% aqueous citric acid (50 ml). Separate the organic layer and wash with saturated aqueous $NaHCO_3$ (100 ml) followed by brine (100 ml). Dry the solution over $Na_2SO_4$, filter and vacuum evaporate the solvent. Triturate the residue with ether (100 ml) and collect the product by filtration. Vacuum dry at room temperature to give the title compound, m.p. 153°–155° C. $R_f$ (silica gel; $CH_2Cl_2$:EtOAc,97:3)=0.40.

(B)
4-Amino-6-Chloro-$N^3$-Methyl-$N^1$-(Phenylmethyl)Benzene-1,3-Disulfonamide Cool a solution of the product of Part A (8.0 g) in THF (50 ml) to 0° C. under a nitrogen atmosphere and add a solution of benzylamine (5.36 g) and triethylamine (5.0 g) dropwise with stirring over 10 minutes. Stir at room temperature for 16 hours and vacuum evaporate the solvent. Partition the residue between EtOAc (250 ml) and 10% aqueous citric acid. Separate the organic layer and wash with water (25 ml) followed by brine (25 ml). Dry the solution over $Na_2SO_4$, filter and vacuum evaporate the solvent. Purify the product by chromatography on a silica gel column eluting with 3% EtOAc in $CH_2Cl_2$. Combine fractions containing the desired product and vacuum evaporate the solvent to obtain the title compound, m.p. 151°–152.5° C. $R_f$ (silica gel; $CH_2Cl_2$: EtoAc, 97:3)=0.20.

(C)
3-(5-Bromopentyl)-6-Chloro-3,4-Dihydro-2-Methyl-7-[(Phenylmethyl)Aminosulfonyl]-2H-1,2,4-Benzothiadiazine S,S-Dioxide Add acetic acid (HOAc) (50 ml) to the product of Part B (5.00 gm) and heat the mixture at 100° C. until a clear solution forms. Cool the solution to 50° C. and immediately add 6-bromohexanal (4.50 gm) followed by 12 N aqueous HCl (2 drops). Stir at room temperature for 16 hours. Collect the solid product by filtration and wash with cold HOAc (10 ml) followed by ether (50 ml). Vacuum dry the product at room temperature to obtain the title compound, m.p. 141°–142° C. $R_f$(silica gel; $CH_2Cl_2$:EtoAc, 97:3)=0.35

(D)
[5-[[6-Chloro-3,4-Dihydro-2-Methyl-7-[(Phenylmethyl)Aminosulfonyl)-2H-1,2,4-Benzothiadiazin-3yl]Pentyl]Ethoxyphosphinyl]Acetic Acid, Ethyl Ester, S, S-Dioxide Heat the product of Part C (2.93 g) to 70° C. under an argon atmosphere and add ethyl (diethoxyphosphino)acetate (3.20 g) with stirring. Heat under an argon atmosphere at 120° C. for 1 hour with stirring. Increase the temperature to 180° C. and maintain this temperature for 3 hours. Remove volatile material under vacuum and chromatograph the residue on a silica gel column eluting with 3% $CH_3OH$ in EtOAc. Combine the desired fractions and vacuum evaporate the solvent to obtain the title compound. $R_f$ (silica gel; EtoAc:$CH_3OH$, 97:3)=0.50

(E)
[5-[[6-Chloro-3,4-Dihydro-2-Methyl-7-[(Phenylmethyl)Aminosulfonyl)-2H-1,2,4-Benzothiadiazin-3-yl]Pentyl]Hydroxyphosphinyl]Acetic Acid, Ethyl Ester, S, S-Dioxide Dissolve the product of Part D (2.50 g) in dry $CH_2Cl_2$ (30 ml) at room temperature under an argon atmosphere. Add bromotrimethylsilane (5.0 ml) and stir for 3 hours at room temperature. Vacuum evaporate the solvent and excess bromotrimethylsilane. Partition the residue between EtOAc (100 ml) and water (25 ml). Separate the organic layer and wash with brine (25 ml). Dry the organic layer over $Na_2SO_4$, filter and vacuum evaporate the solvent. Chromatograph the product on a LH-20 Sephadex column eluting with $CH_3OH$. Combine the desired fractions and vacuum evaporate the solvent to obtain the title compound. $R_f$ (silica gel; $CH_2Cl$:$CH_3OH$: HOAc, 8:1:1)=0.50

(F)
[5-[[6-Chloro-3,4-Dihydro-2-Methyl-7-[(Phenylmethyl)Aminosulfonyl)-2H-1,2,4-Benzothiadiazin-3-yl]Pentyl]Hydroxyphosphinyl]Acetic Acid, S, S-Dioxide Cool a solution of the product of Part E (1.45 g) in THF (10 ml) to 0° C. and add 0.50 N aqueous NaOH (15.0 ml). Stir at room temperature for 18 hours, then vacuum evaporate the solvent. Partition the residue between ethyl acetate (50 ml) and 1 N aqueous HCl (10 ml). Separate the organic layer and wash with water (15 ml) followed by brine (15 ml). Dry the organic solution over $Na_2SO_4$, filter and vacuum evaporate the solvent to obtain the title compound. $R_f$ (silica gel; $CH_2Cl_2$: $CH_3OH$:HoAc, 8:1:1)=0.20

(G)
N-[[5-[[6-Chloro-3,4-Dihydro-2-Methyl-7-[(Phenylmethyl)Aminosulfonyl]-2H-1,2,4-Benzothiadiazin-3-yl]Pentyl]Hydroxyphosphinyl]Acetyl]-N-Cyclopentylglycine, (1,1-Dimethylethyl) Ester, S, S-Dioxide Cool a solution of the product of Part F (0.60 gm) in dry N,N-dimethylformamide (DMF) (10 ml) to 0° C. under an argon atmosphere and add 1,1'-carbonyldiimidazole (0.26 gm) with stirring. After 45 minutes, add triethylamine (0.20 ml) and N-cyclopentylglycine, (1,1-dimethylethyl) ester (0.31 gm). Stir at 0° C. for one hour, then for 18 hours at room temperature. Vacuum evaporate the solvent and partition the residue between EtOAc (30 ml) and 10% aqueous citric acid (10 ml). Separate the organic layer and wash with water (10 ml) followed by brine (10 ml). Dry the organic solution over Na$_2$SO$_4$, filter and vacuum evaporate the solvent. Chromatograph the residue on a LH-20 Sephadex column eluting with CH$_3$OH. Combine the desired fractions and vacuum evaporate the solvent to obtain the title compound. R$_f$ (silica gel; CH$_2$Cl$_2$:CH$_3$OH:HoAc, 8:1:1)=0.40

(H)
N-[[5-[[6-Chloro-3,4-Dihydro-2-Methyl-7-[(Phenylmethyl)Aminosulfonyl]-2H-1,2,4-Benzothiadiazin-3-yl]Pentyl]Hydroxyphosphinyl]Acetyl]-N-Cyclopentylglycine, S, S-Dioxide Cool a solution of the product of Part G (0.40 gm) in CH$_2$Cl$_2$ (5 ml) to 0° C. under an argon atmosphere and add trifluoroacetic acid (5.0 ml) with stirring. Stir at room temperature for 18 hours. Vacuum evaporate the solvent and excess trifluoroacetic acid. Partition the residue between EtOAc (25 ml) and water (5 ml). Separate the organic layer and wash with brine. Dry the solution over Na$_2$SO$_4$, filter and vacuum evaporate the solvent. Chromatograph the residue on a C-18 reverse-phase silica gel column eluting with a linear gradient of CH$_3$OH/H$_2$O (60%→100% CH$_3$OH) containing 0.2% trifluoroacetic acid. Combine the desired fractions and vacuum evaporate the solvent to give 0.32 gm of the title compound. R$_f$ (silica gel, CH$_2$Cl$_2$:CH$_3$OH:HoAc,8:1:1)=0.30.

EXAMPLE 2

1-[[[4-[[[6-CHLORO-3,4-DIHYDRO-2-METHYL-7-[(PHENYLMETHYL)AMINOSULFONYL]-2H-1,2,4-BENZOTHIADIAZIN-3-YL]ACETYL]AMINO]BUTYL]HYDROXYPHOSPHINYL]ACETYL]-CIS,SYNOCTAHYDRO-1H-INDOLE-2(S)-CARBOXYLIC ACID,S,S-DIOXIDE (A) 6-Chloro-3,4-Dihydro-2-Methyl 7-[(Phenylmethyl)Aminosulfonyl]-2H-1,2,4-Benzthiadiazine-3-Acetic Acid, Ethyl Ester, S,S,-Dioxide Add the product of Example 1, Part B (3.0 gm) and ethyl 3,3-diethoxy-propionate to HOAc (50 ml). With stirring, add 12 N aqueous HCl (2 drops) and heat the mixture at 100° C. until a clear solution forms. Stir at room temperature for 16 hours. Collect the solid product by filtration, wash with cold HOAc (20 ml) and vacuum dry to obtain the title compound. R$_f$(silica gel, CH$_2$Cl$_2$ EtOAc; 97:3)=0.40.

(B)
6-Chloro-3,4-Dihydro-2-Methyl-7-[(Phenylmethyl)Aminosulfonyl]-2H-1,2,4-Benzothiadiazine-3-Acetic Acid, S,S-Dioxide Add THF (10 ml) to the product of Part A (1.90 g) and cool in an ice bath. With stirring, add 0.50 N aqueous NaOH (8.0 ml) dropwise. Stir at 0° to 5° C. for 20 hours. Vacuum evaporate the solvent and partition the residue between EtOAc (150 ml) and 0.5 N aqueous HCl (30 ml). Separate the organic layer and wash with water (30 ml) followed by brine (30 ml). Dry the organic solution over Na$_2$SO$_4$, filter and vacuum evaporate the solvent to obtain the title compound, m.p. 141°–145° C.

(C)
1-[[[4-[[[6-Chloro-3,4-Dihydro-2-Methyl-7-[(Phenylmethyl)Aminosulfonyl]-2H-1,2,4-Benzothiadiazin-3yl]Acetyl]Amino]Butyl]Hydroxyphosphinyl]Acetyl]-cis,syn-Octahydro- b 1H-Indole-2(S)-Carboxylic Acid, (1,1-Dimethylethyl)ester, S,S-Dioxide Dissolve the product of Part B (0.46 gm) in DMF (20 ml) and cool the solution to 0° C. under a nitrogen atmosphere. Add 1,1'-carbonyldiimidazole (0.016 gm) and stir at 0° C. for 1 hour. Dissolve 1-[[(4-aminobutyl)hydroxyphosphinyl]acetyl]-cis,syn-octahydro-1H-indole-2(S)-carboxylic acid, (1,1-dimethylethyl)ester (0.37 gm) (See Example 3, Parts A–G) in DMF (25 ml) containing triethylamine (0.10 gm) and add this solution dropwise with stirring to the above cold solution. Stir at 0° C. for 1 hour, then at room temperature for 18 hours. Vacuum evaporate the solvent and partition the residue between EtOAc (50 ml) and 10% aqueous citric acid (1.5 ml). Separate the organic layer and wash with water (10 ml) followed by brine (10 ml). Dry the organic solution over Na$_2$SO$_4$, filter and vacuum evaporate the solvent. Purify the product by chromatography on a LH-20 Sephadex column, eluting with CH$_3$OH. Combine fractions containing the desired product and vacuum evaporate the solvent to obtain the title compound.

D.
1-[[[4-[[[6-Chloro-3,4-Dihydro-2-Methyl-7-[(Phenylmethyl)Aminosulfonyl]-2H-1,2,4-Benzothiadiazin-3yl]Acetyl]Amino]Butyl]Hydroxyphosphinyl]Acetyl]-cis,syn-Octahydro-1H-Indole-2(S)-Carboxylic Acid, S,S-Dioxide Dissolve the product of Part C in CH$_2$Cl$_2$ (15 ml) and cool to 0° C. under a nitrogen atmosphere. Add trifluoroacetic acid (10 ml) and stir at 0° C. for 1 hour followed by 18 hours at room temperature. Vacuum evaporate the solvent and excess trifluoroacetic acid. Partition the residue between EtOAc (50 ml) and water (10 ml). Separate the organic layer and wash with brine. Dry the organic solution over Na$_2$SO$_4$, filter and vacuum evaporate the solvent. Purify the product by chromatography on a C-18 reverse-phase silica gel oolumn, eluting with a linear gradient of CH$_3$OH/H$_2$O (60%→100% CH$_3$OH) containing 0.2% trifluoroacetic acid. Combine the desired fractions and vacuum evaporate the solvent to obtain the title compound.

EXAMPLE 3

1-[[[4-[[[6-CHLORO-3,4-DIHYDRO-3-(2-PHENYLE-THYL)-2H-1,2,4-BENZOTHIADIAZIN-7-YL]SULFONYL]AMINO]BUTYL]HYDROXYPHOSPHINYL]ACETYL]-CIS,SYN-OCTAHYDRO-1H-INDOLE-2(S)-CA RBOXYLIC ACID, S,S-DIOXIDE (A)

[Ethoxy-[4-[2,3-Dihydro-1,3-Dioxo-1H-Isoindol-2-yl]Butyl]Phosphinyl]Acetic Acid, Ethyl Ester Heat 12.5 gm of ethyl (diethoxyphosphino)acetate with 16.9 gm of N-(4-bromobutyl)phthalimide in a melt at 180° for 5 hours under a nitrogen atmosphere. After cooling, chromatograph the mixture on a silica gel column, eluting with a gradient of 1% to 2% $CH_3OH$ in EtOAc. Isolate the major product by vacuum evaporation of the solvent from the combined fractions to obtain the title compound. $R_f$(silica gel; EtOAc:$CH_3OH$, 99:1)=0.40.

(B) [(4-Aminobutyl)Hydroxyphosphinyl]Acetic Acid

Add the product of Part A (30.7 g) to a mixture of 90 ml HOAc, 90 ml 48% HBr, and 45 ml $H_2O$ and heat at reflex with stirring for 22 hours. Evaporate the solution to half volume and cool to give a precipitate of o-phthalic acid. Obtain a second crop by further concentration. Concentrate the filtrate to dryness, take up in 100 ml water, refilter, and extract thoroughly with ether. Evaporate the aqueous layer to dryness in vacuo to give a residue. Take up the residue in water and charge to a column of Bio-Rad AG 50W-X8(H+) cation exchange resin (900 g). Wash the column with deionized water until no further bromide ion is detected in the eluate ($AgNO_3$ test). Elute the column with 10% pyridine in water to give, after solvent removal, the title compound, m.p. 238° C. (dec). $R_f$ (silical gel; BuOH:AcOH:$H_2O$, 3:1:1)=one spot near origin, ninhydrin positive. Mass spectrum [FAB]: M+1 ion at M=196.

(C)

[4-[[(Phenylmethoxy)Carbonyl]Amino]Butyl]Hydroxyphosphinyl]Acetic Acid

Suspend 1.99 g of the product of Part B in 25 ml dry $CH_3CN$, add 10.5 g (10.8 ml) of bis(trimethylsilyl)trifluoroacetamide and stir at room temperature until solids dissolve (approx. 1 hr). Add 2.9 ml benzyl chloroformate and continue stirring at room temperature overnight. Quench the reaction with 10 ml water, then dissolve the product in excess 5% aqueous $NaHCO_3$. Extract the resultant solution with Et20 (3X), acidify the aqueous layer with 10% aqueous HCl, and extract with EtOAc (3X). Wash the combined extracts with water, dry over $MgSO_4$ and evaporate the solvent to obtain a residue. $R_f$ (silica gel; BuOH:HOAc:$H_2O$, 3:1:1)=0.4.

Recrystallize the product from EtoAc to obtain the title compound, m.p. 98°–101° C., FAB mass spec M/e=330 (M+H).

(D)

1-[[[4-[[(Phenylmethoxy)Carbonyl]Amino]Butyl]Hydroxyphosphinyl]Acetyl]-cis,syn-Octahydro-1H-Indole 2(S)-Carboxylic Acid, (1,1-Dimethylethyl)Ester Treat 4.0 g of the product of Part C in 25 ml dry THF at 10° C. with 1.95 g of 1,1'-carbonyldiimidazole. After 30 min., add 3.4 g cis,syn-octahydro-1H-indole-2(S)-carboxylic acid, (1,1-dimethylethyl) ester in 5 ml THF.

Stir the resultant solution overnight at RT. Remove THF in vacuo, and partition the residue between EtOAc and H20. Wash the organic layer with 5% aqueous $KHSO_4$, then extract with 5% $Na_2HPO_4$ (5X). Wash the combined extracts with $Et_2O$, then acidify with cold dilute HCL. Add the precipitate to EtOAc, wash with water and dry over $MgSO_4$. $R_f$ (silica gel; BuOH:HOAC:$H_2O$, 3:1:1)=0.8 FAB mass spec M/e=537 (M+H); M/e=481 (M-isobutylene).

(E)

1-[[(4-Aminobutyl)Hydroxyphosphinyl]Acetyl]-cis,-syn-Octahydro-1H-indole-2(S)-Carboxylic Acid, (1,1-Dimethylethyl)Ester Hydrogenate the product of Part D (1.7 g) at approx. 20 psi over 0.5 g 5% Pd/C in 100 ml absolute ethanol for a total of 5 hours. $R_f$(silica gel; BuOH:HOAc:$H_2O$, 3:1:1)=one spot near origin, ninhydrin positive. Remove catalyst, and evaporate the solvent in vacuo to obtain a residue. FAB mass spec M/e=403 (M+H).

(F)

1-[[[4-[[[6-Chloro-3,4-Dihydro-3-(2-Phenylethyl)-2H-1,2,4-Benzothiadiazin-7-yl]Sulfonyl]Amino]Butyl]Hydroxyphosphinyl]Acetyl]-Cis,Syn-Octahydro-1H-indole2(S) -Carboxylic Acid,(1,1-Dimethylethyl)Ester, S,S-Dioxide Dissolve 0.91 g of the product of Part E, 0.95 g of 6-Chloro-3,4-dihydro-3-(2-phenylethyl)-2H-1,2,4-benzothiadiazine-7-sulfonyl chloride, S,S,-dioxide and 0.7 ml triethylamine in 25 ml dry THF. Stir overnight at RT. Filter off triethylamine HCl. Remove THF in vacuo. Dissolve the resultant residue in water and acidify with a cold 5% $KHSO_4$ solution. Extract with ethyl acetate (3X), water wash extracts and dry over $MgSO_4$. Evaporate the solvent to obtain a residue. Chromatograph the resultant residue on a LH-20 Sephadex Column, eluting with methanol. Combine the desired fractions to obtain the title compound. FAB mass spec M/e=731 (M-isobutylene).

(G)

1-[[[4-[[[6-Chloro-3,4-Dihydro-3-(2-Phenylethyl)-2H-1,2,4-Benzothiadiazin-7-yl]Sulfonyl]Amino]Butyl]Hydroxyphosphinyl]Acetyl]cis,syn-Octahydro-1H-Indole-2(S)-Carboxylic Acid, S,S-Dioxide Dissolve 1.02 g of the product Part F in 25 ml $CH_2Cl_2$, add 3 ml trifluoroacetic acid and stir overnight at RT. Wash the solution with water (4X), once with 5% aqueous citric acid, and again with water. Dry the organic phase over $MgSO_4$ and evaporate the solvent to obtain a residue. Chromatograph the residue on an LH-20 Sephadex column eluting with $CH_3OH$ to obtain the title compound. FAB mass spec M/e=731 (M +1).

EXAMPLE 4

1-[[[4-[[4-[[[[6-CHLORO-3,4-DIHYDRO-3-(2-PHENYLETHYL)-2H-1,2,4-BENZOTHIADIAZIN-7-YL]SULFONYL]AMINO]METHYL]BENZOYL]AMINO]BUTYL]HYDROXYPHOSPHINYL]ACETYL]CIS, SYL-OCTAHYDRO-1H-INDOLE-2(S)-CARBOXYLIC ACID, S,S-DIOXIDE (A) 4-Cyanobenzoic Acid, (1,1-Dimethylethyl) Ester Dissolve 22.1 g 4-cyanobenzoic acid and 28.2 ml t-butanol in 500 ml DMF. Add 9.15 g 4-(dimethylamino) pyridine and 31.5 g 1-(3-dimethylaminopropyl)-3-ethylcarbodiimide hydrochloride. Stir the mixture overnight at RT. Remove the DMF in vacuo, and partition the resultant residue between ethyl acetate and water. Wash the organic layer successively with cold 0.5 N aqueous HCl, water, 5% aqueous NaHC03 and brine. Dry the organic layer over MgSO$_4$ and evaporate the solvent to obtain the title compound. m.p. 75°–78° C. R$_f$(silica gel; 5% EtOAc in hexane)=0.3; IR 2240 cm$^{-1}$; 1730 cm$^{-1}$.

(B) 4-(Aminomethyl)Benzoic Acid, (1,1-Dimethylethyl) Ester

Dissolve 10.1 g of the product of Part A in EtOH (100 ml) saturated with anhydrous NH$_3$. Add 3.0 g 5% Rh on Alumina and hydrogenate at 60 psi overnight at RT. Remove the catalyst and evaporate the solvent to give the title compound. R$_f$ (silica gel; EtOAc)=one major spot near origin, ninhydrin positive.

(C) 4-[[[[6-Chloro-3,4-Dihydro-3-(2-Phenylethyl)-2H-1,2,4-Benzothiadiazin-7-yl]Sulfonyl]Amino]Methyl]Benzoic Acid, (1,1-Dimethylethyl)Ester, S,S, Dioxide Add 10.53. g 6-chloro-3,4-dihydro-3-(2-phenylethyl)-2H-1,2,4-benzothiadiazine-7-sulfonylchloride, S,S-dioxide to a stirred mixture of the product of Part B (5.2 g) and 7.7 ml triethylamine in 50 ml dry THF at 0° C. Stir the mixture at RT for 72 hours. Filter off the triethylamine HCl, and evaporate the solvent. Take up the resultant residue in EtOAc (800 ml) and wash with water, 0.5 N cold aqueous HCl, 5% aqueous NaHCO$_3$ and brine. Dry the organic layer over MgSO$_4$, concentrate to about 300 ml and cool. Collect the solids and wash with cold EtOAc to give the title compound, m.p. 210° C. (dec.) R$_f$ (silica gel; 50% hexane in EtOAc)=0.5. FAB mass spec: M/e=592 (M); M/e=536 (M-isobutylene).

(D) 4-[[[[6-Chloro-3,4-Dihydro-3-(2-Phenylethyl)-2H-1,2,4-Benzothiadiazin-7-yl]Sulfony]Amino]Methyl]Benzoic Acid, S,S, Dioxide Add 6.0 g of the product of Part C to a mixture of 50 ml acetic acid and 5 ml trifluoroacetic acid. Stir for 2 hours at room temperature, then pour into water and collect the precipitate. Water wash the precipitate and vacuum dry to give a residue, m.p. 248°–251° C. (dec.) FAB mass spec; M/e=536 (M).

(E) 1-[[[4-[[4-[[[[6-Chloro-3,4-Dihydro-3-(2-Phenylethyl)-2H-1,2,4-Benzothiadiazin-7-yl]Sulfonyl]Amino]Methyl]Benzoyl]Amino]Butyl]Hydroxyphosphinyl]Acetyl]-cis,syn,-Octahydro-1H-indole-2(S)-Carboxylic Acid,(1,1-Dimethylethyl)Ester S,S-Dioxide Dissolve 2.4 g of the product of Part D in a mixture of 30 ml THF and 3 ml DMF and add a solution of 1,1'-carbonyldiimidazole (0.73 g) in 5 ml THF. After 10 minutes, add a solution of 1.81 g of the product of Example 3, Part E in 10 ml DMF, and stir at room temperature overnight. Remove the solvents in vacuo at 40° C. Partition the resultant residue between 5% aqueous NaHCO$_3$ and EtOAc. Separate the third layer that forms, dissolve it in a large volume of EtOAc, dry over MgSO$_4$, and evaporate the solvent. Chromatograph the resultantresidue on a Sephadex LH-20 column, eluting with methanol to obtain the title compound. R$_f$(silica gel; CH$_2$Cl$_2$:HOAc:CH$_3$OH, 85:7.5:7.5)=0.2. FAB mass spec M/e=943 (M+Na).

(F) 1-[[[4-[[4-[[[[6-Chloro-3,4-Dihydro-3-(2-Phenylethyl)-2H-1,2,4-Benzothiadiazin-7-yl]Sulfonyl]Amino]Methyl]Benzoyl]Amino]Butyl]Hydroxyphosphinyl]Acetyl]-cis,syn-Octahydro-1H-indole-2(S)-Carboxylic Acid, S,S-Dioxide Dissolve 0.92 g of the product of Part E in 3 ml TFA and stir at room temperature for 5 hours. Pour the product into ice water and separate the precipitate. Take up the precipitate in EtOAc, wash with water until neutral to pH paper, dry over MgSO$_4$ and evaporate the solvent to obtain a residue. Dissolve this residue in excess 5% NaHCO$_3$ solution, filter, and reprecipitate with 3N aqueous HCl. Collect the solids, wash and air dry. Dry further in vacuo over P$_2$O$_5$ to obtain the title compound. FAB mass spec: M/e=864 (M).

EXAMPLE 5

1-[[[5-[4-[[[(3-BUTYL-6-CHLORO-3,4-DIHYDRO-2H-1,2,4-BENZOTHIADIAZIN-7-YL)SULFONYL]AMINO]METHYL]PHENYL]PENTYL]HYDROXYPHOSPHINYL]ACETYL]-CIS,SYN-OCTAHYDRO-1H-INDOLE-2(S)-CARBOXYLIC ACID, S,S-DIOXIDE (A) 1-Bromo-5-(4-Cyanophenyl]-4-Pentene Add (4-cyanophenylmethyl)triphenylphosphonium bromide (27.25 g) to dry THF (65 ml) and cool to −20° C. under an argon atmosphere. With stirring, dropwise add 65 ml of a solution of 1 molar lithium bis(trimethylsilyl)amide in THF, maintaining the temperature at −20° C. Stir for 30 minutes at −20° C.; then for 30 minutes at 0° C. Cool to −20° C. and add freshly distilled 4-bromobutanal (10.50 g) dropwise with stirring. Stir at −20° C. for 1 hour, then at room temperature for 16 hours. Remove the solid material by filtration and wash with THF. Vacuum evaporate the solvent from the filtrate and purify the resultant residue by chromatography on silica gel, eluting with CH$_2$Cl$_2$:hexane(4:1). Combine the desired fractions and vacuum evaporate the solvent to obtain the title compound.

(B) 1-Bromo-5-(4-Cyanophenyl)Pentane

Dissolve 5.0 gm of the product of Part A in EtOH (120 ml) and add platinum oxide (0.30 g). Hydrogenate at atmospheric pressure with stirring until one equivalent of hydrogen is consumed. Remove the catalyst by filtration and vacuum evaporate the solvent from the filtrate to obtain the title compound.

(C) [[5-(4-Cyanophenyl)Pentyl]Ethoxyphosphiny]Acetic Acid, Ethyl Ester

Heat the product of Part B (3.50 g) to 70° C. under an argon atmosphere and add ethyl (diethoxyphosphino)acetate (4.00 g) dropwise with stirring. Heat with stirring at 120° C. for 1 hours, then increase the temperature to 180° C. and stir at this temperature for 3 hours. After cooling, purify the product by chromatography on silica gel, eluting with EtOAc:MeOH (97:3). Vacuum evaporate the solvent from the desired fractions to obtain the title compound.

(D)
[[5-[4-(Aminomethyl)Phenyl]Pentyl]Ethoxyphosphinyl]Acetic Acid, Ethyl Ester, Hydrochloride Dissolve 1.70 g of the product of Part C in EtOH (20 ml) containing 8.40 ml of a 4.0 molar solution of anhydrous HCl in dioxane. Add 10% Pd/C (0.1% g) and hydrogenate at 60 psi for 6 hours. Remove the catalyst by filtration and vacuum evaporate the solvent from the filtrate to obtain the title compound.

(E)
[[5-[4-[[[(3-Butyl-6-Chloro-3,4-Dihydro-2H-1,2,4-Benzothiadiazin-7-yl)Sulfonyl]Amino]Methyl]Phenyl]Pentyl]Ethoxyphosphinyl]Acetic Acid, Ethyl Ester, S,S-Dioxide Dissolve 2.0 g of the product of Part D in DMF (20 ml) and cool to −10° C. under a nitrogen atmosphere. With stirring, add triethylamine (3.1 ml) and 3-butyl-6-chloro-3,4-dihydro-2H-1,2,4-benzothiodiazine-7sulfonylchloride, S-S-dioxide (3.3 g). Allow the reaction mixture to warm to room temperature and stir for 16 hours. Vacuum evaporate the solvent and partition the residue between EtOAc (60 ml) and 5% aqueous citric acid (10 ml). Separate the organic phase and wash with 5% aqueous citric acid (10 ml) followed by water (10 ml), and brine (10 ml). Dry the organic solution over $Na_2SO_4$, filter and vacuum evaporate the solvent. Purify the resultant residue by chromatography on silica gel, eluting with $CH_2Cl_2$:EtOAc (7:3). Vacuum evaporate the solvent from the desired fractions to obtain the title compound.

(F)
[[5-[4-[[[(3-Butyl-6-Chloro-3,4-Dihydro-2H-1,2,4-Benzothiadiazin-7-yl]Sulfonyl]Amino]Methyl]Phenyl]Pentyl]Hydroxyphosphinyl]Acetic Acid, Ethyl Ester, S,S-Dioxide Dissolve 1.70 g of the product of Part E in $CH_2Cl_2$ (30 ml) and cool the solution to 0° C. under an argon atmosphere. Add bromotrimethylsilane (5.0 ml) with stirring, allow to warm to room temperature and stir for 3 hours. Vacuum evaporate the solvent and excess bromotrimethylsilane. Partition the residue between EtOAc (70 ml) and water (15 ml). Separate the organic layer and wash with brine (15 ml). Dry the organic solution over $Na_2SO_4$, filter and vacuum evaporate the solvent to obtain the title compound. $R_f$ (silica gel; $CH_2Cl_2$:$CH_3OH$:HOAC, 8:1:1)=0.25.

(G)
[[5-[4-[[[(3-Butyl-6-Chloro-3,4-Dihydro-2H-1,2,4-Benzothiadiazin-7-yl)Sulfonyl]Amino]Methyl]Phenyl]Pentyl]Hydroxyphosphinyl]Acetic Acid, S,S-Dioxide Dissolve 1.52 g of the product of Part F in THF (15 ml) and cool to 0° C. With stirring, add dropwise 0.5 N aqueous NaOH (14.0 ml) and keep at 0° to 5° C. for 18 hours. Vacuum evaporate the solvent and partition the residue between EtOAC (80 ml), and 10% aqueous citric acid (10 ml). Separate the organic layer and wash with water (10 ml) followed by brine (10 ml). Dry the organic solution over $Na_2SO_4$, filter and vacuum evaporate the solvent to obtain the title compound.

(H)
1-[[[5-[4-[[[(3-Butyl-6-Chloro-3,4-Dihydro-2H-1,2,4-Benzothiadiazin-7-yl)Sulfonyl]Amino]Methyl]Phenyl]Pentyl]Hydroxyphosphinyl]Acetyl]-cis,syn-Octahydro-1H-Indole-2(S)-Carboxylic Acid, (1,1-Dimethylethyl)Ester, S,S-Dioxide Dissolve 1.30 g of the product of Part G in DMF (15 ml) and cool to 0° C. under a nitrogen atmosphere. Add 1,1'-carbonyldiimidazole (0.37 g) and stir at 0° C. for 1 hour. With stirring, add triethylamine (0.30 ml) and cis,syn-octahydro-1H-indole 2(S)-carboxylic acid, (1,1dimethylethyl) ester (1.70 g). Stir for 1 hour at 0° C., then at room temperature for 10 hours. Vacuum evaporate the solvent and partition the residue betwen EtOAc (75 ml) and 10% aqueous citric acid (15 ml). Separate the organic phase and wash with water (15 ml) followed by brine (15 ml). Dry the organic solution over $Na_2SO_4$, filter and vacuum evaporate the solvent. Purify the product by chromatography on a LH-20 Sephadex column, eluting with $CH_3OH$. Combine the desired fractions and vacuum evaporate the solvent to obtain the title compound. $R_f$ (silica gel; $CH_2Cl_2$:$CH_3OH$:HOAc, 8:1:1)=0.40.

(I)
1-[[[5-[4-[[[(3-Butyl-6-Chloro-3,4-Dihydro-2H-1,2,4-Benzothiadiazin-7-yl)Sulfonyl]Amino]Methyl]Phenyl]Pentyl]Hydroxyphosphinyl]Acetyl]cis,syn-Octahydro-1H-Indole-2(S)-Carboxylic Acid, S,S,-Dioxide, Hydrate Dissolve 1.32 g of the product of Part H in $CH_2Cl_2$ (15 ml) and cool to 0° C. under a nitrogen atmosphere. Add trifluoroacetic acid (12 ml) and stir at 0° C. for 1 hour, then at room temperature for 16 hours. Vacumm evaporate the solvent and excess trifluoroacetic acid. Partition the residue between EtOAc (60 ml) and water (10 ml). Separate the organic phase and wash with brine. Dry the organic solution over $Na_2SO_4$, filter and vacuum evaporate the solvent. Purify the resultant residue by chromatography on a C-18 reverse-phase silica gel column, eluting with a linear gradient of $CH_3OH$/$H_2O$ (60% →100% $CH_3OH$) containing 0.2% trifluoroacetic acid. Combine the desired fractions and vacuum evaporate the solvent to obtain the title compound. $R_f$ (silica gel; $CH_2Cl_2$:$CH_3OH$:HOAc, 8:1:1)=0.20.

EXAMPLE 6
N-[[[4-[[(3-BUTYL-6-CHLORO-3,4-DIHYDRO-2H-1,2,4-BENZOTHIADIAZIN-7-YL)SULFONYL]AMINO]-4PHENYLBUTYL]HYDROXYPHOSPHINYL]ACETYL]-N-CYCLOPENTYL-GLYCINE,S,S-DIOXIDE (A) 3-Benzoylpropionic Acid,O-Methyloxime Add 3-benzoylpropionic acid (17.82 g) and methoxylamine hydrochloride (9.18 g) to pyridine (250 ml) and heat under a nitrogen atmosphere with stirring at 90° C. for 18 hours. Vacuum evaporate the solvent and add water (50 ml) to the residue. Cool the mixture in an ice bath and add 6N aqueous HCl dropwise with stirring to pH 3. Extract the mixture with EtOAc (3×100 ml) and wash the combined organic extracts with 1N aqueous HCl (50 ml) followed by brine. Dry the EtOAc solution over $Na_2SO_4$, filter and vacuum evaporate the solvent to obtain the title compound.

(B) δ-Aminobenzenebutanol

Cool to −10° C. a solution of product of Part A (20.70 g) in THF (100 ml) under a nitrogen atmosphere. Add dropwise with stirring a 1 molar solution of borane in THF (350 ml) over one hour while maintaining the temperature at −10° C. Stir at −10° C. for one hour, then at room temperature for one hour. Heat the solution at reflux for 18 hours under a nitrogen atmosphere. Cool to −10° C. and add water (75 ml) dropwise with stirring over one hour. Stir at 0° for one hour, then 18 hours at room temperature. Vacuum evaporate the solvent and cool the residue in an ice bath. Add 50% aqueous NaOH (60 g) to the residue dropwise with stirring. Heat the solution at reflux for 4 hours. After cooling, extract the mixture with ether (3×250 ml). Wash the combined extracts with water (50 ml) followed by brine (50 ml). Dry the solution over $Na_2SO_4$, filter and vacuum evaporate the solvent to a volume of 75 ml. Collect the crystalline product by filtration and vacuum dry at room temperature to give the title compound, m.p. 72°–75° C.

(C) 1,3-Dihydro-1,3-Dioxo-δ-Phenyl-2H-Isoindole-2-Butanol

Heat a solution of δ-aminobenzenebutanol (7.32 g), phthalic anhydride (6.57 g) and 4-(dimethylamino)pyridine (0.050 g) in dioxane (100 ml) under a nitrogen atmosphere at reflux for one hour. Evaporate the solvent at atmospheric pressure and heat the residue at 155° C. under a nitrogen atmosphere for 2½ hours. After cooling, dissolve the residue in EtOAc (400 ml). Wash the solution with 10% aqueous citric acid (50 ml) followed by saturated aqueous $NaHCO_3$ (50 ml) and brine (50 ml). Dry the organic layer over $Na_2SO_4$, filter and vacuum evaporate the solvent to obtain the title compound.

(D) 2-(4-Bromo-1-Phenylbutyl)-1H-Isoindole-1,3(2H)-Dione

Cool in an ice bath a solution of triphenylphosphine (19.56 g) in dry $CH_2Cl_2$ (100 ml) under a nitrogen atmosphere. Add carbon tetrabromide (12.37 g) and stir the solution for 10 minutes with cooling. Add a solution of the product of Part C (10.0 g) in dry $CH_2Cl_2$ (100 ml) dropwise with stirring. Stir in an ice bath for one hour then for 18 hours at room temperature. Remove the insoluble material by filtration and vacuum evaporate the filtrate to a volume of 50 ml. Chromatograph the mixture on a silica gel column, eluting with $CH_2Cl_2$. Combine the desired fractions and vacuum evaporate the solvent to obtain the title compound, m.p. 88°–91° C.

(E) [Ethoxy-[4-[2,3-Dihydro-1,3-Dioxo-1H-Isoindol-2-yl]-4-Phenylbutyl]Phosphinyl]Acetic Acid, Ethyl Ester Add ethyl (diethoxyphosphino)acetate (100 ml) to the product of Part D (8.10 g) under an argon atmosphere and heat at 120° C. with stirring for one hour. Increase the temperature to 180° C. and stir at this temperature for 3 hours. After cooling, chromatograph the residue on a silica gel column, eluting with EtOAc:$CH_2Cl_2$(1:1). Combine the desired fractions and vacuum evaporate the solvent to obtain the title compound.

(F) [(4-Amino-4-Phenylbutyl)Hydroxyphosphinyl]Acetic Acid

Add the product of Part E (2.50 g) to a solution of HOAc (11 ml), 33% HBr/HOAc (11 ml) and water (5 ml) and heat with stirring at reflux for 16 hours. Vacuum evaporate the solvents and add water (50 ml) to the residue. Extract with ether (2×30 ml) and add the aqueous phase to a column of AG50WX8(H+) ion-exchange resin (100 ml). Elute with water (200 ml) followed by 10% pyridine in water. Combine the desired fractions and vacuum evaporate the solvent to obtain the title compound. $R_f$ (silica gel; $CHCl_3$:$CH_3OH$:$NH_4OH$, 27:11:2.6)=0.20, (ninhydrin positive).

(G) [[4-[[(3-Butyl-6-Chloro-3,4-Dihydro-2H-1,2,4-Benzothiadiazin-7-yl)Sulfonyl]Amino]-4-Phenylbutyl]Hydroxyphosphinyl]Acetic Acid, S, S-Dioxide Add $CH_3CN$ (25 ml), bis(trimethylsilyl)trifluoroacetamide (4.10 g) and triethylamine (0.40 g) to the product of Part F (1.10 g) under a nitrogen atmosphere. Stir at room temperature for one hour. Add 3-butyl-6-chloro-3,4-dihydro-2H-1,2,4-benzothiadiazine-7sulfonyl chloride,S,S-dioxide (2.25 g) and stir at room temperature for 16 hours. Vacuum evaporate the solvent and extract and purify the resultant residue as described in Example 1, Part C to obtain the title compound. $R_f$ (silica gel; $CH_2Cl_2$:$CH_3OH$,HOAc; 7.5:1:1.5)=0.40.

(H) N-[[[4-[[(3-Butyl-6-Chloro-3,4-Dihydro-2H-1,2,4-Benzothiadiazin-7-yl)Sulfonyl]Amino]-4-Phenylbutyl]Hydroxyphosphinyl]Acetyl]-N-Cyclopentylglycine, (1,1-Dimethylethyl)Ester,S,S-Dioxide Add 1,1'-carbonyldiimidazole (0.26 g) to a solution of the product of Part G (0.80 g) in DMF (10 ml) at 0° C. under an argon atmosphere. Stir at 0° C. for 1 hour, then add triethylamine (0.20 ml) followed by N-cyclopentylglycine, (1,1-dimethylethyl) ester (0.31 gm). Stir at 0° C. for 1 hour, then at room temperature for 16 hours. Vacuum evaporate the solvent, extract and purify the resultant residue as described in Example 1, Part G to obtain the title compound. $R_f$ (silica gel; $CH_2Cl_2$:$CH_3OH$:HOAc, 8:1:1)=0.40.

(I) N-[[[4-[[(3-Butyl-6-Chloro-3,4-Dihydro-2H-1,2,4-Benzothiadiazin-7-yl)Sulfonyl]Amino]-4-Phenylbutyl]Hydroxyphosphinyl]Acetyl]-N-Cyclopentylglycine,S,S-dioxide Dissolve the product of Part H (0.50 g) in $CH_2Cl_2$ (5 ml), cool the solution to 0° C. and add trifluoroacetic acid (5 ml) with stirring. Allow the solution to warm to room temperature and stir for 16 hours. Vacuum evaporate the volatile materials and dissolve the residue in EtOAc (30 ml). Wash the solution with water (10 ml) followed by brine (10 ml). Dry the organic solution over $Na_2SO_4$, filter and vacuum evaporate the solvent. Triturate the residue with ether, collect the solid product by filtration and vacuum dry at room temperature to obtain 0.30 g of the title compound. $R_f$ (silica gel; $CH_2Cl_2$:$CH_3OH$:HOAc, 8:1:1)=0.20.

EXAMPLE 7

1-[[[5-[6-CHLORO-3,4-DIHYDRO-2-METHYL-7-[(PHENYLMETHYL)AMINOSULFONYL]-2H-1,2,4-BENZOTHIADIAZIN-3-YL]PENTYL][(2,2-DIMETHYL-1-OXOPROPOXY)METHOXY]PHOSPHINYL]ACETYL]-CIS,SYN-OCTAHYDRO-1H-INDOLE-2(S)-CARBOXYLIC ACID, S,S-DIOXIDE

A.

1-[[[5-[6-Chloro-3,4-Dihydro-2-Methyl-7-[(Phenylmethyl)Aminosulfonyl]-2H-1,2,4-Benzothiadiazin-3-yl]Pentyl]Hydroxyphosphinyl]Acetyl]-cis,syn-Octahydro-1H-Indole-2(S)-Carboxylic Acid, Phenylmethyl Ester, S,S-Dioxide Following the procedure of Example 1, Part G, substitute 0.41 g of cis,syn-octahydro-1H-indole-2(S)-carboxylic acid, phenylmethylester for N̄-cyclopentylglycine, (1,1dimethylethyl)ester to obtain the title compound.

B.

1-[[[5-[6-Chloro-3,4-Dihydro-2-Methyl-7-[(Phenylmethyl)Aminosulfonyl]-2H-1,2,4-Benzothiadiazin-3-yl]Pentyl][(2,2-Dimethyl-1-Oxopropoxy)Methoxy]-Phosphinyl]Acetyl]-cis,syn-Octahydro-1H-Indole-2(S)-Carboxylic Acid, Phenylmethyl Ester, S,S-Dioxide Dissolve 0.20 g of the product of Part A in DMF (20 ml) containing triethylamine (0.03 g). Add chloromethyl pivalate (0.05 g) and stir at room temperature for 18 hours. Vacuum evaporate the solvent and partition the residue between EtOAc and water. Separate the organic layer and wash with saturated aqueous NaHCO₃, 10% aqueous citric acid and brine. Dry the organic phase over Na₂SO₄, filter and vacuum evaporate the solvent. Chromatograph the residue on silica gel eluting with EtOAc. Combine the desired fractions and vacuum evaporate the solvent to obtain the title compound.

C. Dissolve the product of Part B in EtOH (30 ml) and add 10% Pd/C (0.25 g). Hydrogenate at atmospheric pressure with stirring until one equivalent of hydrogen is consumed. Remove the catalyst by filtration, and vacuum evaporate the solvent to obtain the title compound.

EXAMPLE 8

1-[[[4-[6-CHLORO-3,4-DIHYDRO-2-METHYL-7-[(PHENYLMETHYL)AMINOSULFONYL]-2H-1,2,4-BENZOTHIADIAZIN-3-YL]BUTYL]HYDROXYPHOSPHINYL]ACETYL]-CIS,SYN-OCTAHYDRO-1H-INDOLE-2(S)-CARBOXYLIC ACID,[(2,2-DIMETHYL-1OXOPROPOXY)METHYL]ESTER, S,S-DIOXIDE

A.

1-[(Phenylmethoxy)Carbonyl]-cis,syn-Octahydro-1H-Indole-2(S)-Carboxylic Acid, Ethyl Ester Add cis,syn-octahydro-1H-indole-2(S)-carboxylic acid, ethyl ester d-10-camphorsulfonate (8.01 g) (See Preparation 3, Part B) to THF (50 ml) and cool to 0° C. under a nitrogen atmosphere. Add triethylamine (2.28 ml) with stirring, followed by the dropwise addition of benzyloxycarbonyl chloride (2.86 ml) and additional triethylamine (2.28 ml). Stir the mixture at 0° C. for 4 hours, then at room temperature for 16 hours. Vacuum evaporate the solvent and partition the residue between EtOAc (250 ml) and water (50 ml). Separate the organic layer and wash with saturated aqueous NaHCO₃ (50 ml) followed by water (50 ml) and brine (50 ml). Dry the organic layer over Na₂SO₄, filter and vacuum evaporate the solvent to obtain the title compound as a syrup.

B.

1-[(Phenylmethoxy)Carbonyl]-cis,syn-Octahydro-1H-Indole-2(S)-Carboxylic Acid

Dissolve 7.00 g of the product of Part A in THF (30 ml) and cool to 0° C. Add 1N aqueous NaOH (21.3 ml) and stir at 0° C. for 3 hours, then at room temperature for 16 hours. Vacuum evaporate the solvent and add water (150 ml) to the residue. Extract with ether (2×100 ml) and acidify the aqueous solution to pH 3 with 1NHCl. Extract with EtOAc (2×75 ml) and wash the combined EtOAc extracts with water (25 ml) followed by brine (25 ml). Dry the organic layer over Na₂SO₄, filter and vacuum evaporate the solvent to obtain the title compound.

C.

1-[(Phenylmethoxy)Carbonyl]-cis,syn-Octahydro-1H-Indole-2(S)-Carboxylic Acid [(2,2-Dimethyl-1-Oxopropoxy)Methyl]Ester Dissolve the product of Part B (1.40 g) in THF (30 ml) and cool to 0° C. under a nitrogen atmosphere. Add triethylamine (0.50 g), chloromethyl pivalate (0.77 g) and tetrabutylammonium iodide (0.10 g) and stir at room temperature for 48 hours. Vacuum evaporate the solvent and partition the residue between EtOAc (100 ml) and 10% aqueous citric acid (25 ml). Separate the organic layer and wash with water followed by saturated aqueous NaHCO₃, water and brine. Dry the organic layer over Na₂SO₄, filter and vacuum evaporate the solvent. Purify the product by chromatography on silica gel eluting with CH₂Cl₂:hexane (1:1). Combine the desired fractions and vacuum evaporate the solvent to obtain the title compound.

D. Cis,syn-Octahydro-1H-Indole-2(S)-Carboxylic Acid, [(2,2-Dimethyl-1-Oxopropoxy)Methyl]Ester, p-Toluenesulfonate Dissolve 0.86 g of the product of Part A in EtOAc (20 ml) containing p-toluenesulfonic acid monohydrate (0.39 g). Add 10% Pd/C (0.020 g) and hydrogenate at 45 psi for one hour. Remove the catalyst by filtration and vacuum evaporate the solvent. Vacuum dry the product at room temperature to obtain the title compound.

E. [4-[[6-Chloro-3,4-Dihydro-2-Methyl-7-[(Phenylmethyl)Aminosulfonyl]-2H-1,2,4-Benzothiadiazin-3-yl]Butyl]Hydroxyphosphinyl]Acetic Acid, S, S-Dioxide Using the procedure described in Example 1, Parts A–F, substituting 5-bromopentanal for 6-bromohexanal in Part C, prepare the title compound.

F.

1-[[[4-[6-Chloro-3,4-Dihydro-2-Methyl-7-[(Phenylmethyl)Aminosulfonyl]-2H-1,2,4-Benzothiadiazin-3-yl]Butyl]Hydroxyphosphinyl]Acetyl]-cis,syn-Octahydro-1H-Indole-2(S)-Carboxylic Acid, [(2,2-Dimethyl-1-Oxopropoxy)Methyl]Ester, S,S-Dioxide Dissolve 0.69 g of the product of Part D and 0.88 g of the product of Part E in 7 ml DMF. Stir the solution at room temperature while adding 0.21 g hydroxybenzotriazole hydrate, 1-(3-dimethylaminopropyl)-3-ethylcarbodiimide and 0.23 ml triethylamine. Stir at room temperature overnight, remove the DMF in vacuo and partition the resultant residue between ethyl acetate and water. Wash the organic phase successively with water, 5% citric acid, and water again. Dry the organic layer over MgSO$_4$ and evaporate the solvent to obtain a residue. Chromatograph the residue on a Sephadex LH-20 column, eluting with CH$_3$OH. Combine the desired fractions and evaporate the solvent to obtain the title compound. R$_f$ [silica gel; BuOH:HOAc:H$_2$O, 3:1:1]=0.7; FAB Mass spec: M/e=845 (M+).

EXAMPLE 9

1-[[[4-[6-CHLORO-3,4-DIHYDRO-2-METHYL-7-[(PHENYLMETHYL)AMINOSULFONYL]-2H-1,2,4-BENZOTHIADIAZIN-3-YL]BUTYL]HYDROXYPHOSPHINYL]ACETYL-CIS,SYN-OCTAHYDRO-1H-INDOLE-2(S)-CARBOXAMIDE, S,S-DIOXIDE

A.

1-[(Phenylmethoxy)Carbonyl]-cis,syn-Octahydro-1H-Indole-2-(S)-Carboxamide

Dissolve the product of Example 8, Part B (6.06 g) in DMF (100 ml) and cool the solution to 0° C. under a nitrogen atmosphere. Add 1,1'-carbonyldiimidazole (3.70 g) and stir at 0° C. for one-half hour, then at room temperature for 1 hour. Cool the solution to −20° C. and add concentrated aqueous NH$_4$OH (50 ml) with stirring. Stir at −20° C. for 1 hour, then at room temperature for 2 hours. Vacuum evaporate the solvent and excess NH$_4$OH. Partition the residue between EtOAc (100 ml) and 10% aqueous citric acid. Separate the organic layer and wash with saturated aqueous NaHCO$_3$ followed by brine. Dry the organic solution over Na$_2$SO$_4$, filter and vacuum evaporate the solvent to obtain the title compound.

B. Cis,syn-Octahydro-1H-Indole-2(S)-Carboxamide

Dissolve the product of Part A (4.00 g) in EtOH (30 ml) and add 10% Pd/C (0.10 g). Hydrogenate at 60 psi on a Parr apparatus for 1½ hours at room temperature. Remove the catalyst by filtration and vacuum evaporate the solvent from the filtrate. Vacuum dry the product at room temperature to obtain the title compound, m.p. 116°–118° C.

C. Substituting the product of Part B for the N-cyclopentylglycine ester, carry out the procedures of Example 1, Parts G and H, to obtain the title compound.

Using the procedures described above and substituting the appropriate starting materials, the following compounds may be prepared:

1-[[5-[[6-chloro-3,4-dihydro-2-methyl-7-[(phenylmethyl)aminosulfonyl]-2H-1,2,4-benzothiadiazin-3-yl]pentyl]hydroxyphosphinyl]acetyl]-(S)-proline, S,S-dioxide.

7-[[5-[[6-chloro-3,4-dihydro-2-methyl-7-[(phenylmethyl)aminosulfonyl]-2H-1,2,4-benzothiadiazin-3-yl]pentyl]hydroxyphosphinyl]acetyl]-1,4-dithia-7-azaspiro[4.4]nonane-8(S)-carboxylic acid, S,S-dioxide.

1-[[[4-[[[6-chloro-3,4-dihydro-2-methyl-7-[(phenylmethyl)aminosulfonyl]-2H-1,2,4-benzothiadiazin-3-yl]acetyl]amino]butyl]hydroxyphosphinyl]acetyl]-(S)-proline, S,S-dioxide.

7-[[[4-[[[6-chloro-3,4-dihydro-2-methyl-7-[(phenylmethyl)aminosulfonyl]-2H-1,2,4-benzothiadiazin-3-yl]acetyl]amino]butyl]hydroxyphosphinyl]acetyl]-1,4-dithia-7-azaspiro[4.4]nonane-8(S)-carboxylic acid, S,S-dioxide.

1-[[[4-[[[6-chloro-3,4-dihydro-3-(2-phenylethyl)-2H-1,2,4-benzothiadiazin-7-yl]sulfonyl]amino]butyl]hydroxyphosphinyl]acetyl]-(S)-proline, S,S-dioxide.

7-[[[4-[[[6-chloro-3,4-dihydro-3-(2-phenylethyl)-2H-1,2,4-benzothiadiazin-7-yl]sulfonyl]amino]butyl]hydroxyphosphinyl]acetyl]-1,4-dithia-7-azaspiro[4.4]nonane-8(S)-carboxylic acid, S,S-dioxide.

1-[[[4-[[4-[[[6-chloro-3,4-dihydro-3-(2-phenylethyl)-2H-1,2,4-benzothiadiazin-7-yl]sulfonyl]-mino]methyl]benzoyl]amino]butyl]hydroxyphosphinyl]acetyl]-(S)-proline, S,S-dioxide.

7-[[[4-[[4-[[[6-chloro-3,4-dihydro-3-(2-phenylethyl)-2H-1,2,4-benzothiadiazin-7-yl]sulfonyl]amino]methyl]benzoyl]amino]butyl]hydroxyphosphinyl]acetyl]-1,4-dithia-7-azaspiro[4.4]nonane-8(S)-carboxylic acid, S,S-dioxide.

1-[[[5-[4-[[[[3-butyl-6-chloro-3,4-dihydro-2H-1,2,4-benzothiadiazin-7-yl]sulfonyl]amino]methyl]phenyl]hydroxyphosphinyl]acetyl]-(S)-proline, S,S-dioxide.

7-[[[5-[4-[[[[3-butyl-6-chloro-3,4-dihydro-2H-1,2,4-benzothiadiazin-7-yl]sulfonyl]amino]methyl]phenyl]pentyl]hydroxyphosphinyl]acetyl]-1,4-dithia-7-azaspiro[4.4]nonane-8(S)-carboxylic acid, S,S-dioxide.

1-[[[4-[[[3-butyl-6-chloro-3,4-dihydro-2H-1,2,4-benzothiadiazin-7-yl]sulfonyl]amino]-4-phenylbutyl]hydroxyphosphinyl]acetyl]-(S)-proline, S,S-dioxide.

7-[[[4-[[[3-butyl-6-chloro-3,4-dihydro-2H-1,2,4-benzothiadiazin-7-yl]sulfonyl]amino]-4-phenylbutyl]hydroxyphosphinyl]acetyl]-1,4-dithia-7-azaspiro[4.4]nonane-8(S)-carboxylic acid, S,S-dioxide.

The compounds of this invention are useful in view of their pharmacological properties. In particular, they possess activity as antihypertensive agents, as evidenced by their ability to reduce blood pressure in mammals in which the blood pressure has become abnormally elevated. For example, compounds of this invention lower blood pressure in the spontaneously hypertensive rat (SHR) model.

Compounds of this invention may show activity as diuretic agents.

Since compounds of this invention may also act as angiotensin converting enzyme inhibitors, it is contemplated that they may be used in treating other cardiovascular disorders, for example congestive heart failure, in the same manner as other ACE inhibitors such as captopril and enalapril may be used. In addition, compounds of this invention may be used in the treatment of glaucoma by topical application.

The compounds of this invention can be combined with pharmaceutical carriers and administered in a variety of well-known pharmaceutical forms suitable for oral, parenteral or subcutaneous administration to provide compositions useful in the treatment of cardiovascular disorders and particularly mammalian hypertension.

The daily antihypertensive dose of the compounds of this invention will be typically in the range of about 1 to about 25 mg/kg, of mammalian weight, administered in single or divided doses. The exact dose to be administered is determined by the attending clinician and is dependent upon the potency of the administered compound, i.e. where the particular compound lies within the above range, as well as upon the age, weight and condition of the individual.

Generally, in treating humans having hypertension, the compounds of this invention may be administered to patients in need of such treatment in dosage range of about 5 to about 500 mg per patient generally given several times a day, thus giving a total daily dose of from about 5 to about 2000 mg per day.

The antihypertensive compositions containing the compounds of this invention will preferably contain from about 5 to about 250 mg of the active compound per dosage unit.

The compositions of the present invention are most preferably administered orally. Typical formulations for oral administration are those such as tablets, capsules, syrups, elixirs or suspensions. Typical injectable formulations include solutions and suspensions. Also contemplated are mechanical delivery systems, e.g. transdermal dosage forms.

The typical acceptable pharmaceutical carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinylpyrrolidone, polyvinyl alcohol; alkaline earth metal stearates such as magnesium stearate and calcium stearate; stearic acid; vegetable oils such as peanut oil, cottonseed oil, sesame oil, olive oil and corn oil; non-ionic, cationic and anionic surfactants; ethylene gylcol polymers; beta-cyclodextrin; fatty alcohols and hydrolyzed cereal solids; as well as other non-toxic compatible fillers, binders, disintegrants, buffers, preservatives, anti-oxidants, lubricants, flavoring agents, and the like commonly used in pharmaceutical formulations.

In the following examples the "active ingredient" is N-[[5-[[6-chloro-3,4-dihydro-2-methyl-7-[(phenylmethyl)aminosulfonyl]-2H-1,2,4-benzothiadiazin-3-yl]pentyl]hydroxyphosphinyl]acetyl]-N-cyclopentylglycine, S,S-Dioxide.

It is contemplated, however, that this compound may be replaced by equally effective quantities of other compounds within the scope of formula I.

EXAMPLE 10

| Capsule | Amount (mg) | |
|---|---|---|
| Active ingredient | 250.0 | 125.0 |
| Lactose | 173.0 | 86.5 |
| Corn Starch | 75.0 | 37.5 |
| Magnesium Stearate | 2.0 | 1.0 |
| | 500.00 | 500.00 |

Blend the active ingredient, lactose, and corn starch until uniform; then blend the magnesium sterate into the resulting powder. Encapsulate the mixture into suitably sized two-piece hard gelatin capsules.

EXAMPLE 11

| Tablet | Amount (mg) | |
|---|---|---|
| Active Ingredient | 250.0 | 125.0 |
| Lactose | 161.0 | 80.5 |
| Corn Starch | 12.0 | 6.0 |
| Water (per thousand tablets) | 120. ml (evaporates) | 60 ml (evaporates) |

| Tablet | Amount (mg) | |
|---|---|---|
| Corn Starch | 75.0 | 37.5 |
| Magnesium Stearate | 2.0 | 1.0 |
| | 500.00 | 250.0 |

Blend the active ingredient with the lactose until uniform. Blend the smaller quantity of corn starch with the water and add the resulting corn starch paste, then mix until a uniform wet mass is formed. Add the remaining corn starch to the remaining wet mass and mix until uniform granules are obtained. Screen the granules through a suitable milling machine, using a ¾ inch stainless steel screen. Dry the milled granules in a suitable drying oven until the desired moisture content is obtained. Mill the dried granules through a suitable milling machine using a 16 mesh stainless steel screen. Blend in the magnesium stearate and compress the resulting mixture into tablets of desired shape, thickness, hardness and disintergration.

EXAMPLE 12

| Injectable Solution | mg/ml |
|---|---|
| Active ingredient | 5.00 |
| Methyl p-hydroxybenzoate | 0.80 |
| Propyl p-hydroxybenzoate | 0.10 |
| Disodium Edetate | 0.10 |
| Citric Acid Monohydrate | 0.08 |
| Dextrose | 40.0 |
| Water for injection qs. ad. | 1.0 ml |

Dissolve the p-hydroxybenzoates in a portion of water for injection at 60°-70° C. and cool the solution to 25°-25° C. Charge and dissolve all other excipients and the active ingredient. Bring the solution to final volume, filter it through a sterilizing membrane and fill into sterile containers.

Similarly, substitute other compounds of the present invention to prepare other compositions of the present invention.

We claim:

1. A compound represented by the formula

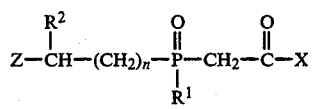

wherein
X is

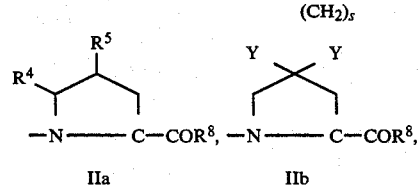

-continued

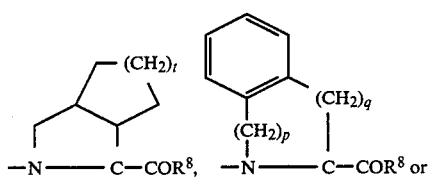
IIc    IId

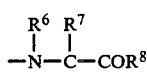
IIe

Y is —S— or —O—;

Z is 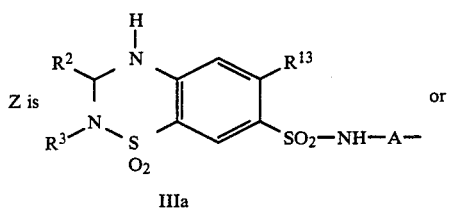 or

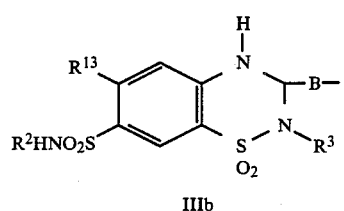
IIIb

A is 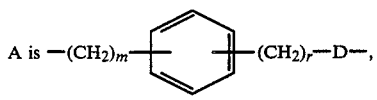,

 or a bond;

B is ,

 or a bond;

D is

or a bond;
m, n, and r are independently 0–14;
x is 1–4;
p and q are independently 0 or 1, provided that the sum of p and q is 1 or 2;
s is 2 or 3;
t is 1–3;
R is hydrogen, lower alkyl, halogen-substituted lower alkyl, cycloloweralkyl, —(CH$_2$)$_u$-cycloloweralkyl, or —(CH$_2$)$_v$—C$_6$H$_5$, wherein u is 1–4 and v is 0–4;
R$^1$ is hydroxy, alkoxy having from 1 to 8 carbon atoms, phenylloweralkoxy, allyloxy, R$^9$—Q- w—(CH$_2$)$_y$—O—, wherein Q is oxygen or sulfur, w is 0 or 1 and y is 2 to 4,

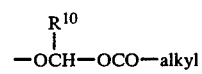

wherein the alkyl has from 3 to 8 carbon atoms,

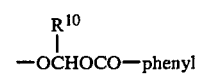

wherein the phenyl may be substituted with group T defined below, 1-glyceryl,

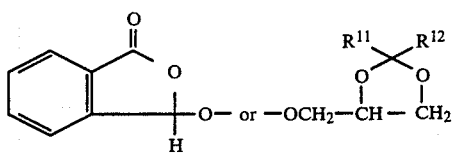

R$^2$ is R or heterocycloloweralkyl, wherein heterocyclo is a 5- or 6-membered aliphatic or aromatic ring of 3 to 5 carbon atoms and 1 to 3 heteroatoms selected from nitrogen, sulfur and oxygen;
R$^3$ is hydrogen or lower alkyl;
R$^4$ and R$^5$ are independently hydrogen, lower alkyl or cycloloweralkyl, or R$^4$ and R$^5$ together with the carbon atoms to which they are attached form a 5- or 6-membered ring;
R$^6$ and R$^7$ are independently hydrogen, lower alkyl or cycloloweralkyl, or R$^6$ and R$^7$ together with the nitrogen and carbon atoms to which they are attached form a 4-, 6-, 7- or 8-membered ring;
R$^8$ is R$^1$, amino, hydroxylamino, mono- or disubstituted amino wherein the substituents are lower alkyl, phenyl or phenylloweralkyl, and wherein the phenyl may be substituted with group T defined below;
R$^9$ is phenyl, substituted phenyl wherein the substituents are chosen from group T, 1-naphthyl or 2-naphthyl;
T is halogen, hydroxy, trifluoromethyl, lower alkoxy, lower alkyl, 2-furanyl, 3-furanyl, 2-thienyl, 3-thienyl, phenyl and substituted phenyl wherein the substituents are chosen from halogen, hydroxy, trifluoromethyl, lower alkoxy or lower alkyl;
R$^{10}$ is hydrogen or alkyl having from 1 to 8 carbon atoms;
R$^{11}$ is hydrogen, lower alkyl, unsubstituted or substituted phenyl and substituted or unsubstituted phenylloweralkyl wherein phenyl may be substituted by group T;
R$^{12}$ is hydrogen or lower alkyl;
R$^{13}$ is chloro or trifluoromethyl;
or a pharmaceutically acceptable salt thereof.

2. A compound of claim 1 wherein Z is represented by formula IIIa.

3. A compound of claim 2 wherein A is

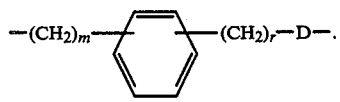

4. A compound of claim 3 wherein D is

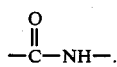

5. A compound of claim 3 wherein D is a bond.
6. A compound of claim 2 wherein A is

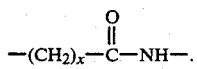

7. A compound of claim 1 wherein Z is represented by formula IIIb.
8. A compound of claim 7 wherein B is

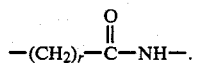

9. A compound of claim 7 wherein B is a bond.
10. A compound of claim 7 wherein B is

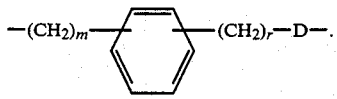

11. A compound of claim 10 wherein D is

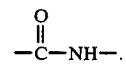

12. A compound of claim 10 wherein D is a bond.
13. A compound of claim 1 wherein X is represented by formula IIa.
14. A compound of claim 1 wherein X is represented by formula IIb.
15. A compound of claim 1 wherein X is represented by formula IIc.
16. A compound of claim 1 wherein X is represented by formula IId.
17. A compound of claim 1 wherein X is represented by formula IIe.
18. A compound of claim 14 wherein each Y is —S—.
19. An antihypertensive pharmaceutical composition comprising an antihypertensive effective amount of a compound of claim 1 together with a pharmaceutically acceptable carrier.
20. A method of reducing blood pressure in hypertensive mammals which comprises administering to a hypertensive mammal a antihypertensive effective amount of a compound of claim 1.
21. A method for reducing blood pressure in an hypertensive mammals which comprises administering to a hypertensive mammal pharmaceutical composition of claim 19.

* * * * *